(12) United States Patent
Kakizawa et al.

(10) Patent No.: US 8,106,100 B2
(45) Date of Patent: Jan. 31, 2012

(54) PROCESS FOR PRODUCING TABLET BY HIGH-SPEED DIRECT COMPRESSION

(75) Inventors: Masayuki Kakizawa, Tokyo (JP); Shunichi Gomi, Tokyo (JP); Yuichi Ozeki, Inabe (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 853 days.

(21) Appl. No.: 12/086,001

(22) PCT Filed: Dec. 5, 2006

(86) PCT No.: PCT/JP2006/324236
§ 371 (c)(1),
(2), (4) Date: Jun. 4, 2008

(87) PCT Pub. No.: WO2007/066646
PCT Pub. Date: Jun. 14, 2007

(65) Prior Publication Data
US 2009/0163604 A1  Jun. 25, 2009

(30) Foreign Application Priority Data
Dec. 6, 2005  (JP) ................................. 2005-352301

(51) Int. Cl.
*A01N 25/00* (2006.01)
*C08B 1/00* (2006.01)
(52) U.S. Cl. .......................................... 514/781; 536/56
(58) Field of Classification Search .......................... None
See application file for complete search history.

(56) References Cited

U.S. PATENT DOCUMENTS

| | | | |
|---|---|---|---|
| 2003/0068367 A1* | 4/2003 | Sowden et al. | 424/464 |
| 2004/0053887 A1* | 3/2004 | Obae et al. | 514/57 |

FOREIGN PATENT DOCUMENTS

| | | |
|---|---|---|
| EP | 1 161 941 A1 | 12/2001 |
| EP | 1 523 994 A1 | 4/2005 |
| JP | 53-127553 | 11/1978 |
| JP | 9-202732 | 8/1997 |
| JP | 2001-10979 | 1/2001 |
| JP | 2001-114703 | 4/2001 |
| JP | 2001-213890 | 8/2001 |
| JP | 2001-347153 | 12/2001 |
| JP | 2003-81876 | 3/2003 |
| JP | 2004-123594 | 4/2004 |
| WO | 00/54752 | 9/2000 |
| WO | 2004/078212 A1 | 9/2004 |

OTHER PUBLICATIONS

Asahi Kasei Chemicals Corp., Ceolus report No. 1, 2003.*
International Search Report (PCT/ISA/210) of International Application PCT/JP2006/324236 (mailed on Jan. 23, 2007).
English language translation of JP 53-127553, Claim 1, Nov. 7, 1978.
The Society of Powder Technology, Japan / Division of Particulate Design and Preparations, Compression Technology of Powder, pp. 44-48, 1998.
Asahi Kasei Corp., Avicel report No. 57, 2002.
Asahi Kasei Chemicals Corp., CEOLUS report No. 1, 2003.
Y. Sagawa, Iyakuhin Seizai Gijutsu, CMC Shuppan, Jul. 25, 2002, pp. 228-229.

* cited by examiner

*Primary Examiner* — Robert A Wax
*Assistant Examiner* — William Craigo
(74) *Attorney, Agent, or Firm* — Staas & Halsey LLP

(57) ABSTRACT

A process for producing a tablet characterized by performing high-speed direct compression with a moving speed of a pestle of 800 mm/s or more while compressing a powder which contains at least 15 to 80% by mass of cellulose, an active ingredient and a lubricant and has an angle of repose of 50° C. or less, a compression degree of 20% or more and an elongation at break of 30 μm or more.

16 Claims, No Drawings

PROCESS FOR PRODUCING TABLET BY HIGH-SPEED DIRECT COMPRESSION

CROSS REFERENCE TO RELATED APPLICATIONS

This application claims the benefit under 35 U.S.C. §371, of PCT International Application No. PCT/JP2006/324236, filed Dec. 5, 2006, which claimed priority to Japanese Application No. 2005-352301 filed Dec. 6, 2005, the contents of which are incorporated herein by reference.

TECHNICAL FIELD

The present invention relates to a process for producing a tablet by high-speed direct compression using a stirring feeder.

BACKGROUND ART

Solid pharmaceutical preparations include tablets, capsules, powders, granules, and so on. Among them, tablets are easily taken and can control a dose of a drug on the basis of the number thereof. Moreover, the tablets are easily handled from production to taking. Therefore, the tablets account for the largest percentage of solid preparations.

Tablets are obtained by supplying a powder as a raw material into a tablet machine and compressing the powder in the tablet machine. Such a tablet machine used is mainly a rotary tablet machine, in which powder supply, compression, and discharge are continuously performed. As the functions of tablet machines have been improved in recent years, upsizing for scaling up tablet machines and speedup for enhancing the rotation speed of tablet machines have been pursued for improving productivity.

So-called high-speed compression, in which compression is performed with a turntable rotated at a high speed, is performed at an enhanced die/punch moving speed for a shortened packing time of a powder to be compressed in a die. Therefore, there is concern about poor packability and increased tablet weight variation.

Non-Patent Document 1 discloses that the flowability of a powder subjected to compression must conventionally be as favorable as possible for obtaining tablets having small weight variation in high-speed compression, and a powder of which an angle of repose or a compressibility used as an index for the flowability is as small as possible is preferably used.

Therefore, high-speed compression is generally performed by adopting a method called wet granulation which involves granulating a raw material powder with a binder solution or water to prepare heavy granules having a small angle of repose and a small compressibility and then performing compression. Examples thereof include techniques described below.

Patent Document 1 discloses a process for producing a tablet, which involves compressing a powder containing 2 to 30% by weight of powder cellulose by wet granulation. This document discloses that the granules have an angle of repose of 35 to 42°, and granules having an angle of repose exceeding 42° cause large tablet weight variation.

Patent Document 2 discloses a technique for compressing a granulated aggregate containing 95% by weight or more of sugar alcohol. This document discloses that the granulated aggregate of sugar alcohol has an angle of repose of 40° or less, and granules having an angle of repose exceeding 40° are not preferable because of problems such as poor flowability, increased variation in packability into a die during compression, and increased tablet weight variation.

Patent Document 3 discloses a technique for granulating trehalose for compression. This document discloses that a compressibility as a standard by which flowability is determined is 40% or less, and powders having a compressibility exceeding 40% have poor flowability and cause large tablet weight variation.

Patent Document 4 discloses a technique for producing a compressed product, which involves granulating a drug, polyethylene oxide, and a granulating agent to obtain a granular powder. This document discloses that a compressibility is calculated as an index for the flowability of the granular powder and is preferably 15% or less, more preferably 10% or less.

However, the wet granulation method requires many processes such as powder mixing, granulation, drying, size selection, and compression, and energy and cost required therefore are increased. Moreover, process validation must be performed according to the number of processes. The process validation means "documented evidence with a high degree of certainty that a process will consistently produce a product meeting its predetermined specification and quality characteristics". A larger number of processes requires a larger number of process validations and therefore requires additional labor and cost. Thus, the wet granulation method has, for the above-mentioned reasons, the disadvantage that it requires cost.

On the other hand, a direct compression method, which involves mixing a powder of an ingredient to be compressed and then directly supplying the powder into a tablet machine to produce a tablet, requires a smaller number of processes and apparatuses than those required for the wet granulation method that has often been used so far. Hence, this method requires low production cost and is known as an advantageous production process from time, energy, and process validation viewpoints.

However, in direct compression, a powder is directly supplied into a tablet machine and compressed. Therefore, it has been considered that the flowability of the powder determined using an angle of repose or a compressibility as an index directly influences tablet weight variation during compression. Therefore, the direct compression method tends to cause larger weight variation than that by the wet granulation method. Particularly, for high-speed compression performed for a short supply time of a powder into a die, there is concern about further increased weight variation.

Thus, it has generally been considered that in the direct compression method as well, a powder of which an angle of repose and a compressibility are as small as possible must be prepared for improving the flowability of the powder, as in the wet compression method. Methods for obtaining a powder for compression having a small angle of repose and a small compressibility include the use of an excipient having a small angle of repose and a small compressibility and a method which involves adding a fluidizer such as light anhydrous silicic acid (Aerosil (trade name)).

Patent Document 5 discloses an excipient for direct compression. This document discloses that the excipient for direct compression has an angle of repose of 35 to 42°, and also discloses that the excipient for direct compression having an angle of repose exceeding 42° causes a bridge in a hopper due to insufficient flowability which inhibits the discharge of a pharmaceutical composition from the hopper and also causes large tablet variation, and such an excipient is thus impossible to use in high-speed direct compression.

Patent Document 6 discloses a technique for improving the flowability of a powder, which involves adding a fluidizer such as light anhydrous silicic acid as a surface modifying base material to a medicinal ingredient and mixing them to obtain a surface-modified powder containing the medicinal ingredient. This document discloses that the surface-modified powder containing the medicinal ingredient has excellent flowability corresponding to an angle of repose of 42° or less, preferably 40° or less and therefore permits tablet production by direct compression.

As described above, a powder having a large angle of repose and a large compressibility has been judged as having poor flowability and considered to increase weight variation during high-speed direct compression. Therefore, the idea has been unexpected that such a powder is used as a powder for high-speed direct compression, and in some cases, is more suitable for the high-speed direct compression.

However, most excipients for direct compression having a small angle of repose and a small compressibility generally have low compactibility. Therefore, such an excipient, when applied to high-speed direct compression performed for a short compression time, is likely to cause problems such as insufficient hardness of tablets or compression failures such as capping. Moreover, a fluidizer has the disadvantage that it is very bulky and has very poor handleability. The addition thereof may reduce binding properties or dissolution behavior. Furthermore, even the addition of the fluidizer brings about limited improvement in flowability. The addition of the fluidizer in large amounts rather presents problems such as poor flowability of a powder.

On the other hand, means for reducing weight variation of tablets obtained by direct compression from a powder having a large angle of repose, a large compressibility, and poor flowability includes a stirring feeding method which involves placing a stirring feeder in the proximity of a supply portion into a die in the lower part of a hopper and forcibly supplying a powder into the die while compacting the powder. This method has the effect of reducing weight variation, as compared with an open feeding method in which a powder for compression is supplied into a die only by gravitation. However, it has been considered that in the stirring feeding method as well, a powder for compression of which an angle of repose and a compressibility are as small as possible must be prepared for reducing weight variation. Furthermore, in the stirring feeding method as well, higher-speed compression leads to a shorter packing time into a die. Therefore, it has been considered that a powder having a large angle of repose and a large compressibility is also unsuitable for the high-speed compression using a stirring feeder.

Thus, in direct compression, it has been known that the use of an excipient for direct compression having high compactibility is effective for enhancing the hardness of tablets or preventing compression failures such as capping or sticking. However, such an excipient for direct compression having high compactibility generally has a large angle of repose and a large compressibility. Therefore, such an excipient has been considered to be unsuitable for direct compression, particularly, high-speed direct compression and has the limited purpose of use.

For example, the excipient for direct compression is typified by crystalline cellulose. Crystalline cellulose having very high compactibility (e.g., CEOLUS (registered trademark) KG-802) is effective for the compression of low compactible drugs, and the like. However, such crystalline cellulose having high compactibility has insufficient flowability and has often been used so far such that: the crystalline cellulose is added in an amount small enough not to exert harmful influence on flowability; and the crystalline cellulose, when added in large amounts absolutely necessary for securing compactibility, is compressed at a low speed using a stirring feeder, while a fluidizer is added for improving flowability as much as possible. Only in high-speed direct compression limited to formulations having no problem of tablet compactibility, crystalline cellulose having good flowability but low compactibility (e.g., CEOLUS PH-102 or PH-302) has often been used.

Non-Patent Document 2 discloses a direct compression technique using CEOLUS KG-802. However, a compression speed in this document is merely 590 mm/s in terms of a punch moving speed and is less than a speed for a high-speed compression on a production scale. Moreover, compression is performed by adding Aerosil as a fluidizer for improving the flowability of an excipient so as to improve the flowability (angle of repose and compressibility) of a powder as much as possible.

Non-Patent Document 3 discloses a direct compression technique by a stirring feeding method also using CEOLUS KG-802. In this document, a compression speed is set to a speed in consideration of a production scale. However, compression at a much higher compression speed is desired in light of the current level of tablet machines. Moreover, this document is based on the conventional idea that the angle of repose and compressibility of a powder having poor flowability are reduced as much as possible by optimizing the amount of light anhydrous silicic acid (Aerosil) added as a fluidizer and its mixing time so as to reduce weight variation. The idea is unexpected therein that a powder suitable for high-speed direct compression using a stirring feeder is prepared. Moreover, a CV value as an index for the weight variation of tablets is 1%, which is also close to the upper limit acceptable in production. Therefore, further rise in compression speed cannot be expected.

Patent Document 1: JP-A-2001-347153
Patent Document 2: JP-A-2001-10979
Patent Document 3: JP-A-2001-213890
Patent Document 4: Pamphlet of WO 04/78212 (EP-A-1523994)
Patent Document 5: JP-A-53-127553
Patent Document 6: Pamphlet of WO 00/54752 (EP-A-1161941)
Non-Patent Document 1: The Society of Powder Technology, Japan/Division of Particulate Design and Preparations, Compression Technology of Powder, pp. 44-48
Non-Patent Document 2: Asahi Kasei Corp., Avicel report No. 57, 2002
Non-Patent Document 3: Asahi Kasei Chemicals Corp., CEOLUS report No. 1, 2003

DISCLOSURE OF THE INVENTION

An object of the present invention is to provide a process for producing a tablet by high-speed direct compression using a stirring feeder.

The present inventors have conducted diligent studies and have consequently completed the present invention by finding out that tablets having small weight variation and high hardness are obtained by performing high-speed compression at a punch moving speed of 800 mm/s or more, while compacting, with a stirring feeder, a powder which comprises at least 15 to 80% of crystalline cellulose, an active ingredient, and a lubricant, has an angle of repose of 50° or less, a compressibility of 20% or more, and a tensile elongation at break of 30 to 100 μm, and requires flow energy of 400 mJ or less during aeration.

Specifically, the present invention is as follows:

(1) A process for producing a tablet, characterized by comprising performing high-speed direct compression at a punch moving speed of 800 mm/s or more, while compacting a powder which comprises at least 15 to 80% by mass of cellulose, an active ingredient, and a lubricant and has an angle of repose of 50° or less, a compressibility of 20% or more, and a tensile elongation at break of 30 μm or more.

(2) The process according to (1), wherein the cellulose is crystalline cellulose of which an average degree of polymerization is 150 to 450, a rate of particles remaining on a sieve of 250 μm in mesh size is 10% by mass or less, average L/D of particles of 75 μm or smaller is 2.0 or more, a bulk density is 0.25 g/cm$^3$ or less, and an angle of repose is 43° or more.

(3) The process according to (1) or (2), wherein the powder requires flow energy of 400 mJ or less during aeration.

(4) The process according to (3), wherein the powder requires flow energy of 350 mJ or less during aeration.

(5) The process according to (1) or (2), wherein the powder has an angle of repose of 30 to 50°.

(6) The process according to (1) or (2), wherein the powder has a compressibility of 20 to 50%.

(7) The process according to (1) or (2), wherein the powder has a tensile elongation at break of 100 μm or less.

(8) The process according to (3) or (4), wherein the powder requires flow energy of 100 mJ or more during aeration.

(9) The process for producing a tablet according to any one of (1) to (3), wherein the compaction is performed with a stirring feeder attached to a tablet machine.

(10) A tablet obtained by the process according to any one of (1) to (9).

(11) A powder composition for high-speed direct compression available in the process according to any one of (1) to (9), which comprises at least 15 to 80% by mass of cellulose, an active ingredient, and a lubricant and has an angle of repose of 50° or less, a compressibility of 20% or more, and a tensile elongation at break of 30 μm or more.

(12) Crystalline cellulose for high-speed direct compression available in the process according to any one of (1) to (9), of which an average degree of polymerization is 150 to 450, a rate of particles remaining on a sieve of 250 μm in mesh size is 10% by mass or less, average L/D of particles of 75 μm or smaller is 2.0 or more, a bulk density is 0.25 g/cm$^3$ or less, and an angle of repose is 43° or more.

The production process of the present invention has the advantageous effect that tablets having small weight variation and high hardness can be obtained in high-speed direct compression.

BEST MODE FOR CARRYING OUT THE INVENTION

Hereinafter, the present invention will be described specifically.

A powder of the present invention comprises cellulose. Examples of the cellulose include crystalline cellulose, powder cellulose, and cellulose derivatives such as hydroxypropyl cellulose and low-substituted hydroxypropyl cellulose. The amount of the cellulose added is 15 to 80% by mass, preferably 20 to 60% by mass. When the amount of the cellulose added is 15% by mass or less, effects brought about by the addition of the cellulose are not obtained. Therefore, such an amount is not preferable. Alternatively, when the amount of the cellulose-added exceeds 80% by mass, the resulting powder for compression is bulky and has poor handleability. Therefore, such an amount is not preferable.

Moreover, the powder of the present invention comprises an active ingredient. The active ingredient described in the present invention refers to a powder of a pharmaceutical medicinal ingredient, an agrochemical ingredient, a fertilizer ingredient, a feed ingredient, a food ingredient, a cosmetic ingredient, a dye, a flavor, a metal, a ceramic, a catalyst, a surfactant, or the like and may be in any form such as a powder, a crystal, an oil, or a solution.

Examples of the powder of the pharmaceutical medicinal ingredient include those administered orally, such as antipyretic analgesic antiphlogistics, hypnotic sedatives, sleepiness inhibitors, antidinic drugs, infant analgesics, stomachics, antacids, digestives, cardiotonics, drugs for arrhythmia, hypotensive drugs, vasodilators, diuretics, antiulcer drugs, drugs for controlling intestinal function, therapeutic drugs for osteoporosis, antitussive expectorants, antiasthmatics, antibacterial drugs, therapeutic drugs for pollakiuria, tonics, and vitamin preparations.

Moreover, in the present invention, the powder may optionally be supplemented with other additives such as excipients, disintegrants, binders, fluidizers, flavoring substances, flavors, coloring agents, sweeteners, and surfactants.

Examples of the excipients include: sugars such as white sugar, glucose, lactose, fructose, and maltose; sugar alcohols such as mannitol, xylitol, maltitol, erythritol, and sorbitol; starches such as rice starch, wheat starch, corn starch, and potato starch; and inorganic matters such as calcium hydrogen phosphate, calcium carbonate, anhydrous silicic acid, hydrous silicic acid, aluminum silicate, calcium silicate, and magnesium aluminosilicate.

Examples of the disintegrants include: celluloses such as croscarmellose sodium, carmellose calcium, carmellose, and low-substituted hydroxypropyl cellulose; starches such as sodium carboxymethyl starch, hydroxypropyl starch, and partly pregelatinized starch; and crospovidone and the like.

Examples of the binders include: water-soluble polysaccharides such as gelatin, pullulan, carrageenan, locust bean gum, agar, konjac mannan, xanthan gum, tamarind gum, pectin, sodium alginate, and gum arabic; celluloses such as hydroxypropyl cellulose, hydroxypropylmethyl cellulose, and methyl cellulose; starches such as pregelatinized starch and starch paste; and synthetic polymers such as polyvinylpyrrolidone, carboxy vinyl polymer, and polyvinyl alcohol.

Examples of the fluidizers include hydrated silicon dioxide and light anhydrous silicic acid. Examples of the flavoring substances include glutamic acid, fumaric acid, succinic acid, citric acid, sodium citrate, tartaric acid, malic acid, ascorbic acid, sodium chloride, and l-menthol.

Examples of the flavors include orange, vanilla, strawberry, yoghurt, and menthol. Examples of the coloring agents include: food dyes such as food red No. 3, food yellow No. 5, and food blue No. 1; and riboflavin. Examples of the sweeteners include aspartame, saccharin, dipotassium glycyrrhizinate, and stevia. Examples of the surfactants include phospholipids, glycerin fatty acid esters, polyethylene glycol fatty acid esters, sorbitan fatty acid esters, and polyoxyethylene hydrogenated castor oil.

The powder comprising crystalline cellulose, an active ingredient, and additives is made uniform by a mixing procedure. The mixing procedure is performed using a technique known in the art, for example, mixing in a plastic bag, mixing using a rotary vessel-type low-speed mixer, or mixing using a high-speed stirring mixer.

The rotary vessel-type low-speed mixer is a mixer in which a powder is lifted by the rotation of a vessel itself around the axis attached to the vessel and dropped by gravitation so as to mix the powder. Such a mixer mainly performs the mixing of the powder by movement and diffusion. Examples of types of such rotary vessel-type mixers include V-type mixers, double cone-type mixers, tumbler-type mixers, horizontal cylinder-type mixers, inclined cylinder-type mixers, cubic-type mixers, conical-type mixers, and Y-cone-type mixers.

Examples of the high-speed stirring mixer include surface modification apparatuses, high-speed mixers, high-speed stirring-type mixing granulators, and universal blenders. Examples of specific apparatuses include Mechanomill (trade name, manufactured by Okada Seiko Co., Ltd.), Vertical Granulator (trade name, manufactured by Powrex Corp.), High-Speed Mixer (trade name, manufactured by Fukae Powtec Co., Ltd.), and Laboratory Matrix (trade name, manufactured by Nara Machinery Co., Ltd.).

The size of the mixer can be determined arbitrarily according to the amount of a powder supplied into a tablet machine.

The mixing time of the powder may usually be a time required for uniformly mixing the powder and is preferably approximately 5 to 60 minutes.

A lubricant is further added to the thus-mixed powder comprising an active ingredient, crystalline cellulose, and optionally additives. Examples of the lubricant used in the present invention include magnesium stearate, calcium stearate, stearic acid, sucrose fatty acid esters, and talc. The amount of the lubricant added is preferably 0.1 to 3 parts by weight with respect to 100 parts by weight of the powder comprising crystalline cellulose, an active ingredient, and additives.

A mixing procedure for the lubricant is performed using a technique known in the art, for example, mixing in a plastic bag or mixing using a rotary vessel-type low-speed mixer. A high-speed stirring mixer causes reduction in compactibility due to the excessive mixing of the lubricant and therefore, is not preferable. A mixing time is preferably approximately 1 to 15 minutes.

The powder obtained by the above-mentioned procedures is used to perform high-speed direct compression during compaction.

The high-speed direct compression used in the present invention will be described. A tablet machine used is a rotary tablet machine. The rotary tablet machine is a tablet machine comprising a die and a punch equally arranged in a concentric configuration on a turntable and having a mechanism in which the packing of a powder from a hopper, the compression of the powder, and the discharge of tablets are continuously performed by the rotation of the turntable. Among them, a two-stage compression tablet machine is preferable which performs compression at two stages of precompression and main compression. Alternatively, a multistage compression tablet machine or the like may be used which performs two or more or continuous precompressions. Alternatively, a single tablet machine may be used which performs one cycle involving packing, compression, and discharge during one rotation of a turntable, or a double tablet machine may be used which performs two such cycles during one rotation of a turntable.

The high-speed direct compression of the present invention refers to direct compression performed at a punch moving speed of 800 mm/s or more, preferably 1000 mm/s or more, in terms of a linear velocity. The punch moving speed is determined from the rotational diameter of a punch on a turntable of a rotary tablet machine and the number of revolutions according to the formula:

Punch moving speed [mm/s]=π×(rotational diameter of punch [mm])×(the number of revolutions [s$^{-1}$]).

Moreover, the compaction performed during the high-speed direct compression of the present invention means that a powder dropped from a hopper portion serving as a powder receiver is forcibly compacted, when packed in a compression die. Examples of methods thereof include a method which involves forcibly pressing a powder into a die through a partial space below a stirring blade while rotating the stirring blade, and specifically include a method which involves performing compaction using a stirring feeder attached to a tablet machine, and a method which involves: temporally packing a powder having a redundancy in excess of a set tablet mass into a die; allowing packing density varying along dies to converge to a constant value using an apparatus for applying a weak compression force; leveling off the powder so that the volume thereof corresponds to the set tablet mass; discharging the redundancy; and then performing compression. The use of a stirring feeder attached to the tablet machine permits the direct use of a rotary tablet machine without modifying it. Therefore, compaction using such a stirring feeder is preferable.

There is no particular upper limit on the punch moving speed. The punch moving speed is preferably a speed at which a powder is sufficiently supplied into a die even with a stirring feeder, and is preferably 3000 mm/s or less, more preferably 2000 mm/s.

Examples of shapes of the stirring blade of the stirring feeder include comb-like and flat forms. The number of blades is 1, 2, 3, etc. The maximum rotation speed provided by one stirring blade (linear velocity at the periphery of the stirring blade) is 150 mm/s or more, preferably 200 mm/s or more, particularly preferably 300 mm/s or more, though differing depending on the shape, size, and the like of the blade. When the maximum rotation speed is less than 150 mm/s, a compaction force for forcibly pressing a powder does not sufficiently work. Therefore, such a speed is not preferable.

Moreover, the shapes of the die and the punch used in the production process of the present invention are not particularly limited and may be selected from circular, oval, triangular, square or rectangular, pentagonal, hexagonal, and astral forms, and the like. Circular forms are particularly preferable from the viewpoint of handleability in use. Moreover, the diameters of the die and the punch in circular forms in the tablet machine may be sizes that permit the production of usual pharmaceutical tablets and are preferably 6 to 20 mm, more preferably 6 to 10 mm. Moreover, the shape of a compression surface of the punch may be a shape that permits the production of usual pharmaceutical tablets. A flat punch, an R punch, a double R punch, a punch with a cleavage line, or the like can be used. Alternatively, a stamping punch may be used. A material for the punch may be a material usually used. The compression surface may be coated with metal plating such as chromium coating or may be polished with an abrasive for use. Moreover, the weight of a tablet obtained by compression may fall within a range that can be used as a usual tablet.

The powder used in the high-speed direct compression of the present invention has an angle of repose of 50° or less, preferably 47° or less, more preferably 45° or less. The angle of repose is measured by a method described later in Examples. When the angle of repose exceeds 50°, the resulting powder has poor handleability before compression such that it causes clogging during transport or causes a bridge in a hopper. Therefore, such an angle of repose is not preferable. The angle of repose of 50° or less is a necessary condition for securing such handleability. In conventional techniques, it has been considered that a smaller angle of repose achieves better powder flowability and smaller weight variation during compression. However, such an idea of the conventional techniques does not necessarily apply to the high-speed direct compression performed during compaction using a stirring feeder. The angle of repose is preferably 35° or more, more preferably 38° or more, most preferably 40° or more.

Moreover, the powder used in the high-speed direct compression of the present invention has a compressibility of 20% or more. The compressibility is measured by a method described later in Examples.

The detailed reason why the powder having a compressibility of 20% or more is suitable for the high-speed direct compression performed during compaction using a stirring feeder is unknown. However, this may be because: most powders having a compressibility of 20% or more are bulky in a loose state; and thus, such powders uniformly contain air in compaction using a stirring feeder and therefore easily flow when packed in a die through the stirring feeder. In conventional techniques, it has been considered, as described above, that a powder having a lower compressibility has better flowability, and the compressibility serves as an index for reduction in weight variation during high-speed compression. However, it was demonstrated that such a conventional idea does not apply to the high-speed direct compression performed during compaction.

Moreover, a powder having too a large compressibility has poor handleability such that it causes clogging during transport or causes a bridge in a hopper. Thus, the compressibility is preferably 60% or less, more preferably 50% or less.

Moreover, the powder used in the high-speed direct compression of the present invention must have a tensile elongation at break of 30 μm or more and preferably 30 to 100 μm. In this context, the tensile elongation at break described in the present invention will be described. The tensile elongation at break is measured using a powder layer compression characteristic/tensile rupture characteristic testing apparatus "Agrobot" (trade name, manufactured by Hosokawa Micron Corp.). A powder to be measured is packed to a height of 40 mm (volume: 19.6 cm$^3$) in a cell of 25 mm in inside diameter, and the amount of the powder packed is weighed. Then, the cell is tapped 50 times. The powder is compressed in a compression test portion at a compression speed of 0.1 mm/s for a compression retention time of 60 s using a maximum compression set value of 300 N, and then measured in a tensile test portion at a pulling speed of 0.4 mm/s for a sampling time for pulling of 25 s. A tensile strength at break and a tensile elongation at break are determined from the maximum tensile strength at break and a displacement thereof during this test, respectively.

The tensile elongation at break of 30 μm or more means that powders having such a tensile elongation at break are difficult to separate from each other.

When a tensile strength at break and a tensile elongation at break of the powder for high-speed direct compression having a tensile elongation at break of 30 μm or more are also measured after passing through a stirring feeder used in compression, the tensile elongation at break tends to increase. Powders having such a tensile elongation at break are difficult to separate from each other even after passing through a stirring feeder. Hence, the powders having a tensile elongation at break of 30 μm or more are difficult to separate from each other and uniformly retain air. The powders, when packed into a die using a stirring feeder, are pressed in a portion of the die where the lower punch is moved downward. In this procedure, the powders having a tensile elongation at break of 30 μm or more uniformly retain air without being separated from each other and are packed in this state into the die. Therefore, such powders packed therein produce small weight variation and achieve reduced weight variation even in the high-speed direct compression. On the contrary, when the tensile elongation at break is less than 30 μm, powders having such a tensile elongation at break are easily separated from each other. Therefore, such powders may be scattered with a stirring feeder and become difficult to compact in a die. Moreover, such powders are separated from each other and cannot uniformly retain air. Therefore, an air loophole occurs and locally produces a powder density difference. Thus, weight variation of powders packed into a die during high-speed direct compression is increased. Therefore, such a tensile elongation at break is not preferable.

On the other hand, when the tensile elongation at break is too large, powders having such a tensile elongation at break are very difficult to separate from each other and therefore, do not flow, resulting in poor handleability. Such powders may have problems such as the blockage of a hopper outlet. Therefore, the tensile elongation at break is preferably 100 μm or less.

The flowability of a powder used in compression has conventionally been evaluated based on an index measured, so to speak, in a static state, such as an angle of repose or a compressibility. The powder used in the high-speed direct compression of the present invention has also been judged as having poor flowability and considered to be unsuitable for application to high-speed direct compression, when evaluated using a static index for flowability. Hence, the idea has been unexpected that the powder of the present invention is used in high-speed direct compression for the purpose of reducing weight variation.

However, the present inventors have found out the use of the tensile elongation at break as such an index and found out for the first time that a powder that meets this index is appropriate for the high-speed direct compression performed during compaction.

The cellulose used in the present invention is preferably crystalline cellulose. The crystalline cellulose is preferably crystalline cellulose of which an average degree of polymerization is 150 to 450, a rate of particles remaining on a sieve of 250 μm in mesh size is 10% by mass or less, average L/D of particles of 75 μm or smaller is 2.0 or more, a bulk density is 0.25 g/cm$^3$ or less, and an angle of repose is 43° or more, more preferably crystalline cellulose of which average L/D of particles of 75 μm or smaller is 2.0 to 4.5, a bulk density is 0.10 to 0.25 g/cm$^3$, and an angle of repose is 47 to 60°, most preferably crystalline cellulose of which average L/D of particles of 75 μm or smaller is 2.0 to 3.5, a bulk density is 0.14 to 0.25 g/cm$^3$, and an angle of repose is 47 to 55°. For example, a commercially available product CEOLUS (registered trademark) KG-802 (Asahi Kasei Chemicals Corp.) can be used.

When the average degree of polymerization is less than 150, the resulting cellulose has insufficient compactibility and does not impart hardness to a tablet. Therefore, such an average degree of polymerization is not preferable. When the average degree of polymerization exceeds 450, the resulting cellulose becomes strongly fibrous and has remarkably poor flowability. Therefore, such an average degree of polymerization is not preferable. Particles of 250 μm or larger form a close-grained structure and have insufficient compactibility. Therefore, when the rate of particles remaining on a sieve of 250 μm in mesh size exceeds 10% by mass, such a rate of particles is not preferable. When the average L/D of particles of 75 μm or smaller is less than 2.0; the bulk density exceeds 0.25 g/cm$^3$; or the angle of repose is less than 43°, the resulting cellulose has insufficient compactibility in any case and does not permit high-speed direct compression performed during compaction using a stirring feeder. Therefore, such an item is not preferable.

Moreover, for preventing the cellulose from becoming strongly fibrous and having poor handleability, the average L/D of cellulose particles of 75 μm or smaller is preferably 4.5 or less; the bulk density is preferably 0.10 g/cm$^3$ or more; and the angle of repose is preferably 60° or less.

Moreover, the powder used in the high-speed direct compression of the present invention requires flow energy of preferably 400 mJ or less, more preferably 350 mJ or less, even more preferably 100 to 350 mJ, during aeration.

In this context, the flow energy during aeration will be described. The flow energy during aeration is measured using a powder flowability analyzer "Powder Rheometer FT4" (trade name, distributed by Sysmex Corp.). 160 mL of a powder is packed into an exclusive 160-mL split vessel so that the powder is leveled off. Then, a rotary torque and a vertical load required for moving a blade downward in the powder at a speed of 30 mm/s with the blade rotated at a speed of 100 mm/s are measured, and an integration value thereof is defined as the amount of energy required for the blade to push its way through the powder layer and used as an index for flowability. A smaller amount of energy gives the blade lower resistance. The resulting powder can be said to be a good powder.

After one measurement, the blade goes up to the original position, while it is rotated backward at a speed of 40 mm/s. This procedure is repeated 7 times after packing. Then, air is introduced at a linear velocity of 1 mm/s into the powder layer from beneath so that the powder incorporates the air therein. Energy required for moving the blade downward in the powder at a speed of 30 mm/s with the blade rotated at a speed of 100 mm/s is measured in the same way, and this energy is defined as the flow energy during aeration described in the present invention.

It is considered that the powder requiring flow energy of 400 mJ or less during aeration lightly incorporates air therein and is easily moved. This may mean that such a powder uniformly incorporates air therein, when passing through a stirring feeder, and has good flowability. On the contrary, when the flow energy during aeration is larger than 400 mJ, the resulting powder cannot incorporate air therein, and the air easily comes out thereof, resulting in possible debasement in powder flowability. Therefore, such flow energy during aeration is not preferable.

The present inventors have found out that the flowability of a powder passing through a stirring feeder is reflected more accurately in flow energy during aeration, rather than an angle of repose or a compressibility, and found out for the first time that a powder that meets particular conditions about a tensile elongation at break and flow energy during aeration used as indexes produces small weight variation during high-speed direct compression performed during compaction using a stirring feeder and is appropriate for the high-speed direct compression.

In this context, the flow energy during aeration is preferably 100 mJ or more. When the flow energy during aeration is less than 100 mJ, the resulting powders tend to flow too much, when passing through a stirring feeder, and rather cause separation. Therefore, such flow energy during aeration is not preferable.

In high-speed compression using a stirring feeder, the packing density of the powder used in the high-speed direct compression of the present invention into a die undergoes compaction effects brought about by the stirring feeder. Therefore, the packing density is larger than a loose bulk density of the powder for high-speed direct compression before passing thorough the feeder and is 1.35 times the loose bulk density.

The loose bulk density of the powder for high-speed compression before passing through the feeder refers to a loose bulk density obtained in compressibility measurement described later in Examples.

The packing density into a die will be described. The packing density into a die is determined from the weight and volume of a powder packed into a compression die as follows:
(Compression Conditions)

Rotary tablet machine (LIBRA2, manufactured by Kikusui Seisakusho Ltd.)

Turntable: rotational diameter: 410 mm, the number of revolutions: 80 rpm (punch moving speed: 1720 mm/s)

The number of punches: 12 used among 36 punches (repetitions of 1 per set and 2 blank caps)

Tablet shape: 8 mm in diameter, circular, 12R

Tablet weight: 180 mg

Compression pressure: precompression: 3.5 kN, main compression: 7 kN

Stirring feeder: stirring feeder attached to LIBRA2 (comb-like blades of 210 mm in diameter, 2 per set), the number of revolutions: 60 rpm (linear velocity at the periphery: 660 mm/s)
(Weight of Powder Packed in Die)

The weight [g] of a powder packed into a die is defined as the same weight as that of a tablet obtained by compressing the powder and determined as an average value of 20 tablets.
(Volume of Powder Packed into Die)

Moreover, the volume of a powder packed into a die is determined from the diameter [cm] of the die, the set depth [cm] from the leveling portion of the die to a lower punch, and the volume of a hollow in a punch according to the formula (1):

$$\text{Volume [cm}^3\text{] of powder packed into die}=\pi\times[0.5\times(\text{diameter [cm] of die})]^2\times(\text{set depth [cm] to lower punch})+(\text{volume [cm}^3\text{] of hollow in punch}) \quad (1)$$

The volume of the hollow in a punch is calculated from the shape and size of the punch. For example, when a flat punch is used, the volume of its hollow is 0. When an R punch having a diameter of 8 mm and a radius of curvature of 12 mm is used, the volume of a hollow in the punch is 0.0174 cm$^3$.
(Packing Density into Die)

Thus, the packing density into a die is defined according to the formula (2):

$$\text{Packing density into die [g/cm}^3\text{]}=(\text{average weight [g] of 20 tablets/volume [cm}^3\text{] of powder packed into die}) \quad (2)$$

The packing density into a die thus determined is 1.35 times or more the loose bulk density of the powder for high-speed direct compression before passing thorough the feeder.

This supports that the powder used in high-speed direct compression is sufficiently compacted, when packed into a die through a stirring feeder. When the powder is sufficiently largely compacted, the packability of the powder is influenced more strongly by a compaction force acting on the powder than by factors determined depending on conditions during compression, such as the flowability of the powder itself, its weight, and a compression speed. Therefore, such high-speed direct compression, which is performed at a large punch moving speed for a short packing time, can reduce weight variation because of packing largely depending on compaction.

Moreover, usual compression has poorer packability of a powder into a die with increases in compression speed and therefore tends to have smaller packing density into a die. However, compression using the powder of the present invention is characterized in that even high-speed compression performed at a punch moving speed of 800 mm/s or more has no difference in packing density into a die from low-speed compression performed at a punch moving speed less than 800 mm/s.

Low-speed direct compression performed at a punch moving speed less than 800 mm/s can compress any powder into tablets having small weight variation, because of its long packing time. High-speed direct compression having no difference in packing density into a die from the low-speed compression leads to the same packability as that in the low-speed compression, that is, weight variation that can be kept as small as that in the low-speed compression.

(Packing Density into Die During Low-Speed Compression)

The packing density into a die during low-speed compression is determined into the same way as in the determination of the packing density into a die during high-speed direct compression except that the number of revolutions of a turntable is decreased to 30 rpm (punch moving speed: 640 mm/s). This packing density into a die during low-speed compression is compared with the packing density into a die during high-speed compression.

In this comparison, when the powder for high-speed direct compression of the present invention is used, "the packing density during high-speed compression/the packing density during low-speed compression" is 0.98 or more. This means that the packability of the powder during high-speed compression is favorable, as in the low-speed compression.

EXAMPLES

Hereinafter, the present invention will be described specifically with reference to Examples and Comparative Examples. However, the present invention is not intended to be limited to them.

First, methods for measuring properties will be described.

1) Angle of Repose [°]

A powder was dropped through a metal funnel of 0.8 cm in orifice diameter using a powder property tester (manufactured by Hosokawa Micron Corp., Powder Tester T-R model (trade name)) under conditions involving a vibration scale of 1.5, and the angle between a horizontal plane and a ridge of the piled powder (measured for the angles of two ridges, measurement distance: 3°) was measured. The angle of repose was indicated in an average value from three measurements.

2) Compressibility [%]

The compressibility was determined according to the formula:

Compressibility [%]=[(packed bulk density−loose bulk density)/packed bulk density]×100.

(1) Loose Bulk Density [g/cm$^3$]

The loose bulk density was measured with Powder Tester manufactured by Hosokawa Micron Corp. by: uniformly supplying a sample into a cylindrical vessel of 5.03 cm in diameter and 5.03 cm in height (volume: 100 ml) from 23 cm above through a JIS 22-mesh (710 µm) sieve; leveling off the top surface of the sample; and weighing its weight.

(2) Packed Bulk Density [g/cm$^3$]

The packed bulk density was measured by: putting an exclusive cap provided as an accessory of Powder Tester manufactured by Hosokawa Micron Corp. in the upper part of this vessel after loose bulk density measurement; further adding the sample up to the upper edge of the cap; tapping the vessel 180 times from a height of 1.8 cm; then removing the cap; and leveling off the sample at the position of the upper surface of the vessel; and weighing the amount of the sample packed into the 100-ml vessel.

3) Tensile Elongation at Break [µm]

(1) Measurement

A powder layer compression characteristic/tensile rupture characteristic testing apparatus "Agrobot" (manufactured by Hosokawa Micron Corp.) was used. A powder to be measured was packed to a height of 40 mm (volume: 19.6 cm$^3$) in a cell of 25 mm in inside diameter, and the amount of the powder packed was weighed. Then, the cell was tapped approximately 50 times. The powder was compressed in a compression test portion at a compression speed of 0.1 mm/s for a compression retention time of 60 s using a maximum compression set value of 300 N, and then measured in a tensile test portion at a pulling speed of 0.4 mm/s for a sampling time for pulling of 25 s. The maximum tensile strength at break and a displacement thereof during this test were defined as a tensile strength at break and a tensile elongation at break, respectively.

(2) Measurement of Powder after Passing Through Stirring Feeder

A tablet machine was operated under the following conditions:

Rotary tablet machine (LIBRA2 (trade name), manufactured by Kikusui Seisakusho Ltd.)

Turntable: rotational diameter: 410 mm, the number of revolutions: 30 rpm (rotation speed: 640 mm/s)

The number of punches: 0 (blank cap)

Stirring feeder: stirring feeder attached to LIBRA2 (comb-like blades of 210 mm in diameter, 2 per set), the number of revolutions: 60 rpm (linear velocity at the periphery: 660 mm/s).

A powder passing through the stirring feeder without being compressed was collected and used in the above-mentioned measurement of (1).

4) Average Degree of Polymerization of Cellulose

The value was measured by the copper ethylenediamine solution viscosity method described in the crystalline cellulose identification test (3) in the Japanese Pharmacopoeia, 14th edition.

5) Rate of Cellulose Particles Remaining on Sieve of 250 µm in Mesh Size [%]

10 g of a sample was sifted through a JIS standard sieve (Z8801-1987) of 250 µm in mesh size for 10 minutes using a Ro-tap sieve shaker (Sieve Shaker A model manufactured by Taira Koseisakusho, Ltd.), and the mass of particles remaining on the sieve of 250 µm in mesh size was indicated in percentage with respect to the whole mass of the sample.

6) Average L/D of Cellulose Particles of 75 µm or Smaller

A light microscopic image of particles that had passed through a JIS standard sieve of 75 µm in mesh size in shifting using Air Jet Sieve (manufactured by ALPINE, A200LS model) was subjected to image analysis processing (manufactured by Interquest Inc., apparatus: Hyper 700, software: Imagehyper). L/D of the particles was defined as the ratio between the long and short sides (long side/short side) of a rectangle having the smallest area among rectangles circumscribed about each of the particles. Average L/D of the particles was determined as an average value from at least 400 particles. This measurement must be conducted by previously letting the individual particles spread out without being entangled.

7) Bulk Density of Cellulose [g/cm$^3$]

The bulk density of cellulose was measured with Powder Tester manufactured by Hosokawa Micron Corp. by: uniformly supplying a sample into a cylindrical vessel of 5.03 cm in diameter and 5.03-cm in height (volume: 100 ml) from 23 cm above through a JIS 22-mesh (710 μm) sieve; leveling off the top surface of the sample; and weighing its weight.

8) Angle of Repose of Cellulose [°]

A powder was dropped through a metal funnel of 0.8 cm in orifice diameter using a powder property tester (manufactured by Hosokawa Micron Corp., Powder Tester T-R model) under conditions involving a vibration scale of 1.5, and the angle between a horizontal plane and a ridge of the piled powder (measured for the angles of two ridges, measurement distance: 3°) was measured. The angle of repose was indicated in an average value from three measurements.

9) Flow Energy During Aeration [mJ]

A powder flowability analyzer Powder Rheometer FT4 (manufactured by Sysmex Corp.) was used. 160 mL of a powder was packed into an exclusive 160-mL split vessel so that the powder was leveled off. Then, a rotary torque and a vertical load required for moving a blade downward in the powder with the blade rotated at a speed of 100 mm/s were measured, and an integration value thereof was defined as the amount of energy required for the blade to push its way through the powder layer and used as an index for flowability.

After one measurement, the blade went up to the original position, while it was rotated backward at a speed of 40 mm/s. This procedure was repeated 7 times after packing. Then, air was introduced at a linear velocity of 1 mm/s into the bottom of the powder layer so that the powder incorporated the air therein. Energy required for moving the blade downward in the powder with the blade rotated at a speed of 100 mm/s was measured in the same way, and this energy was defined as the flow energy during aeration described in the present invention.

10) Packing Density into Die [g/cm³]

(1) Compression Conditions

Rotary Tablet Machine (LIBRA, Manufactured by Kikusui Seisakusho Ltd.)

Turntable: rotational diameter: 410 mm, the number of revolutions: 80 rpm (punch moving speed: 1720 mm/s)

The number of punches: 12 used among 36 punches (repetitions of 1 per set and 2 blank caps)

Tablet shape: 8 mm in diameter, circular, 12R

Tablet weight: 180 mg

Compression pressure: precompression: 3.5 kN, main compression: 7 kN

Stirring feeder: stirring feeder attached to LIBRA2 (comb-like blades of 210 mm in diameter, 2 per set), the number of revolutions: 60 rpm (linear velocity at the periphery: 660 mm/s).

(2) Weight of Powder Packed in Die

The weight [g] of a powder packed in a die was defined as the same weight as that of a tablet obtained by compressing the powder and determined as an average value from 20 tablets.

(3) Volume of Powder Packed in Die

Moreover, the volume of a powder packed in a die is determined from the diameter [cm] of the die, the set depth [cm] from the leveling portion of the die to a lower punch, and the volume of a hollow in a punch according to the formula (1):

$$\text{Volume [cm}^3\text{] of powder packed in die} = \pi \times [0.5 \times (\text{diameter [cm] of die})]^2 \times (\text{set depth [cm] to lower punch}) + (\text{volume [cm}^3\text{] of hollow in punch}) \quad (1)$$

The volume of the hollow in a punch is calculated from the shape and size of the punch. For example, when a flat punch is used, the volume of its hollow is 0. When an R punch having a diameter of 8 mm and a radius of curvature of 12 mm is used, the volume of a hollow in the punch is 0.0174 cm³.

(4) Packing Density into Die

Thus, the packing density into a die is defined according to the formula (2):

$$\text{Packing density into die [g/cm}^3\text{]} = (\text{average weight [g] of 20 tablets/volume [cm}^3\text{] of powder packed in die}) \quad (2)$$

When the use of an open feeder is specified in Comparative Examples, compression was conducted under the same conditions as the compression conditions of (1) except that an open feeder attached to LIBRA2 was used instead of using a stirring feeder, and the bulk density was determined according to (2) to (4).

11) Packing Density During High-Speed Compression/Packing Density During Low-Speed Compression The packing density measured in 10) was defined as the packing density during high-speed compression.

The packing density during low-speed compression was measured under the same conditions as the compression conditions of 10) except that the number of revolutions of a turntable was decreased to 30 rpm (punch moving speed: 640 mm/s).

In this way, the ratio of the packing density during high-speed compression/the packing density during low-speed compression was determined.

When the use of an open feeder is specified in Comparative Examples, compression was conducted under the same conditions as the compression conditions of (1) except that an open feeder attached to LIBRA2 was used instead of using a stirring feeder.

12) Process for Producing Tablet

In Examples and Comparison Examples, compression was performed under the following conditions to obtain tablets, unless otherwise specified:

(Tablet Machine Conditions)

Rotary Tablet Machine (LIBRA, Manufactured by Kikusui Seisakusho Ltd.)

Turntable: rotational diameter: 410 mm, the number of revolutions: 60 rpm (rotation speed: 1290 mm/s)

The number of punches: a group of 36 punches

Tablet shape: 8 mm in diameter, circular with a sharp edge

Tablet weight: 180 mg

Compression pressure: precompression: 5 kN, main compression: 10 kN

Stirring feeder: accessory of LIBRA (comb-like blades of 210 mm in diameter, 2 per set), the number of revolutions: 60 rpm (linear velocity at the periphery: 660 mm/s)

Compression time: 3 hours (388000 tablets in total, 70.0 kg)

When the use of an open feeder is specified in Comparative Examples, compression was conducted under the same conditions as the compression conditions of (1) except that an open feeder attached to LIBRA was used instead of using a stirring feeder.

13) Measurement of Weight Variation

Tablets were sampled 8 times from 1 hour to 3 hours after the start of compression at 15-minute intervals (on 75, 90, 105, 120, 135, 150, 165, and 180 min.). The weights of 10 tablets sampled at each point in time were measured. A weight CV value (%) in each sampling was calculated from the average value and standard deviation of each group and used as an index for weight variation.

$$\text{Weight CV value in each sampling} = (\text{standard deviation/average value}) \times 100 \, [\%]$$

An average value from the weight CV values of the eight sampled groups was used as an index for weight variation.

14) Hardness of Tablet (N)

1 day after compression, the tablets obtained by the compression of 12) were broken under load in the diameter direction of the tablets, and this load was measured using a Schleuniger hardness tester (manufactured by Freund Industrial Co., Ltd.). The hardness was indicated in an average value from 10 samples.

15) Rate [%] of Reduction in Hardness of Tablet

The tablets obtained by the compression of 12) were stored for 1 month in a plastic bag (11.5 mm×9 mm, moisture permeability: 3 to 5 g/m² (24 Hr)) with a zipper under conditions involving 40° C. and 75% R.H. The hardness of the tablets after this storage was measured in the same way as in 14). The rate of reduction in hardness of tablet was determined according to the formula:

100−(hardness of tablet after 1 month/hardness of tablet determined 1 day after compression)×100.

Example 1

28.5 kg of crystalline cellulose CEOLUS KG-802 (trade name, manufactured by Asahi Kasei Chemicals Corp.; average degree of polymerization: 270, rate of particles remaining on a sieve of 250 µm in mesh size: 1% by mass, average L/D of particles of 75 µm or smaller: 3.0, bulk density: 0.196 g/cm³, and angle of repose: 500) as cellulose, 5.0 kg of acetaminophen (manufactured by API Corp.) as an active ingredient, and 66.5 kg of granulated lactose SUPER-TAB (trade name, distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for use in high-speed direct compression.

The powder thus obtained had an angle of repose of 42°, a loose bulk density of 0.454 g/cm³, a packed bulk density of 0.628 g/cm³, and a compressibility of 28%. Moreover, the powder had a tensile elongation at break of 45 µm and required flow energy of 307 mJ during aeration.

A portion of this powder was used to measure a tensile elongation at break of the powder after passing through a stirring feeder, packing density into a die, and packing density during low-speed compression. As a result, the tensile elongation at break of the powder after passing through a stirring feeder was 70 µm; the packing density into a die was 1.51 times the loose bulk density; and the ratio of "the packing density during high-speed compression/the packing density during low-speed compression" was 0.998. The present powder was sufficiently compacted with the stirring feeder during high-speed compression.

The remaining powder was used and compressed for 3 consecutive hours using a rotary tablet machine (LIBRA) to obtain tablets, which were evaluated. The average value of weight CV values of the tablets was 0.54%; the hardness of the tablets was 92 N; and the rate of reduction in the hardness of the tablets was 12%. The results are shown in Table 1.

Example 2

47.5 kg of crystalline cellulose CEOLUS KG-802 (manufactured by Asahi Kasei Chemicals Corp.; average degree of polymerization: 270, rate of particles remaining on a sieve of 250 µm in mesh size: 1% by mass, average L/D of particles of 75 µm or smaller: 3.0, bulk density: 0.196 g/cm³, and angle of repose: 50°) as cellulose, 5.0 kg of acetaminophen (manufactured by API Corp.) as an active ingredient, and 47.5 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for use in high-speed direct compression.

The powder thus obtained had an angle of repose of 45°, a loose bulk density of 0.328 g/cm³, a packed bulk density of 0.509 g/cm³, and a compressibility of 36%. Moreover, the powder had a tensile elongation at break of 67 µm and required flow energy of 256 mJ during aeration.

A portion of this powder was used to measure a tensile elongation at break of the powder after passing through a stirring feeder, packing density into a die, and packing density during low-speed compression. As a result, the tensile elongation at break of the powder after passing through a stirring feeder was 82 µm; the packing density into a die was 1.61 times the loose bulk density; and the ratio of "the packing density during high-speed compression/the packing density during low-speed compression" was 0.981. The present powder was sufficiently compacted with the stirring feeder during high-speed compression.

The remaining powder was used and compressed for 3 consecutive hours using a rotary tablet machine (LIBRA) to obtain tablets, which were evaluated. The average value of weight CV values of the tablets was 0.59%; the hardness of the tablets was 104 N; and the rate of reduction in the hardness of the tablets was 10%. The results are shown in Table 1.

Example 3

25.5 kg of crystalline cellulose CEOLUS KG-802 (manufactured by Asahi Kasei Chemicals Corp.; average degree of polymerization: 270, rate of particles remaining on a sieve of 250 µm in mesh size: 1% by mass, average L/D of particles of 75 µm or smaller: 3.0, bulk density: 0.196 g/cm³, and angle of repose: 50°) as cellulose, 15.0 kg of acetaminophen (manufactured by API Corp.) as an active ingredient, and 59.5 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for use in high-speed direct compression.

The powder thus obtained had an angle of repose of 43°, a loose bulk density of 0.411 g/cm³, a packed bulk density of 0.623 g/cm³, and a compressibility of 34%. Moreover, the powder had a tensile elongation at break of 44 µm and required flow energy of 288 mJ during aeration.

A portion of this powder was used to measure a tensile elongation at break of the powder after passing through a stirring feeder, packing density into a die, and packing density during low-speed compression. As a result, the tensile elongation at break of the powder after passing through a stirring feeder was 62 µm; the packing density into a die was 1.56 times the loose bulk density; and the ratio of "the packing density during high-speed compression/the packing density during low-speed compression" was 0.988. The present powder was sufficiently compacted with the stirring feeder during high-speed compression.

The remaining powder was used and compressed for 3 consecutive hours using a rotary tablet machine (LIBRA) to obtain tablets, which were evaluated. The average value of weight CV values of the tablets was 0.58%; the hardness of the tablets was 85 N; and the rate of reduction in the hardness of the tablets was 8%. The results are shown in Table 1.

Comparative Example 1

28.5 kg of crystalline cellulose CEOLUS PH-302 (trade name, manufactured by Asahi Kasei Chemicals Corp.; average degree of polymerization: 140, rate of particles remaining on a sieve of 250 µm in mesh size: 1% by mass, average L/D of particles of 75 µm or smaller: 1.3, bulk density: 0.417 g/cm$^3$, and angle of repose: 380) as cellulose, 5.0 kg of acetaminophen (manufactured by API Corp.) as an active ingredient, and 58.5 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for use in compression.

The powder thus obtained had an angle of repose of 33°, a loose bulk density of 0.629 g/cm$^3$, a packed bulk density of 0.729 g/cm$^3$, and a compressibility of 14%. Moreover, the powder had a tensile elongation at break of 17 µm and required flow energy of 415 mJ during aeration.

A portion of this powder was used to measure a tensile elongation at break of the powder after passing through a stirring feeder, packing density into a die, and packing density during low-speed compression in the same way as in Example 1. As a result, the tensile elongation at break of the powder after passing through a stirring feeder was 10 µm; the packing density into a die was 1.25 times the loose bulk density; and the ratio of "the packing density during high-speed compression/the packing density during low-speed compression" was 0.971. The present powder was not sufficiently compacted even with the stirring feeder in high-speed compression.

The remaining powder was used and compressed for 3 consecutive hours using a rotary tablet machine (LIBRA) in the same way as in Example 1 to obtain tablets, which were evaluated. The average value of weight CV values of the tablets was 0.74%; the hardness of the tablets was 72 N; and the rate of reduction in the hardness of the tablets was 17%. The results are shown in Table 1.

The powder in this example was thought to be a powder having good flowability because of its smaller angle of repose and smaller compressibility than those of the powders of Examples 1 to 3. However, the tablets obtained from this powder had large weight variation during compression and low hardness.

Comparative Example 2

28.5 kg of crystalline cellulose CEOLUS PH-102 (trade name, manufactured by Asahi Kasei Chemicals Corp.; average degree of polymerization: 250, rate of particles remaining on a sieve of 250 µm in mesh size: 0.2% by mass, average L/D of particles of 75 µm or smaller: 1.3, bulk density: 0.312 g/cm$^3$, and angle of repose: 40°) as cellulose, 5.0 kg of acetaminophen (manufactured by API Corp.) as an active ingredient, and 58.5 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for use in compression.

The powder thus obtained had an angle of repose of 34°, a loose bulk density of 0.511 g/cm$^3$, a packed bulk density of 0.702 g/cm$^3$, and a compressibility of 28%. Moreover, the powder had a tensile elongation at break of 28 µm and required flow energy of 406 mJ during aeration.

A portion of this powder was used to measure a tensile elongation at break of the powder after passing through a stirring feeder, packing density into a die, and packing density during low-speed compression in the same way as in Example 1. As a result, the tensile elongation at break of the powder after passing through a stirring feeder was 30 µm; the packing density into a die was 1.29 times the loose bulk density; and the ratio of "the packing density during high-speed compression/the packing density during low-speed compression" was 0.972. The present powder was not sufficiently compacted even with the stirring feeder in high-speed compression.

The remaining powder was used and compressed for 3 consecutive hours using a rotary tablet machine (LIBRA) in the same way as in Example 1 to obtain tablets, which were evaluated. The average value of weight CV values of the tablets was 0.73%; the hardness of the tablets was 78 N; and the rate of reduction in the hardness of the tablets was 15%. The results are shown in Table 1.

The powder in this example was thought to be a powder having good flowability because of its smaller angle of repose and smaller compressibility than those of the powders of Examples 1 to 3. However, the tablets obtained from this powder had large weight variation during compression and low hardness.

Comparative Example 3

28.5 kg of crystalline cellulose CEOLUS PH-200 (trade name, manufactured by Asahi Kasei Chemicals Corp.; average degree of polymerization: 230, rate of particles remaining on a sieve of 250 µm in mesh size: 15.8% by mass, average L/D of particles of 75 µm or smaller: 1,2, bulk density: 0.357 g/cm$^3$, and angle of repose: 35°) as cellulose, 5.0 kg of acetaminophen (manufactured by API Corp.) as an active ingredient, and 58.5 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for use in compression.

The powder thus obtained had an angle of repose of 32°, a loose bulk density of 0.548 g/cm$^3$, a packed bulk density of 0.650 g/cm$^3$, and a compressibility of 16%. Moreover, the powder had a tensile elongation at break of 6 µm and required flow energy of 491 mJ during aeration.

A portion of this powder was used to measure a tensile elongation at break of the powder after passing through a stirring feeder, packing density into a die, and packing density during low-speed compression in the same way as in Example 1. As a result, the tensile elongation at break of the powder after passing through a stirring feeder was 1 μm; the packing density into a die was 1.18 times the loose bulk density; and the ratio of "the packing density during high-speed compression/the packing density during low-speed compression" was 0.962. The present powder was not sufficiently compacted even with the stirring feeder in high-speed compression.

The remaining powder was used and compressed for 3 consecutive hours using a rotary tablet machine (LIBRA) in the same way as in Example 1 to obtain tablets, which were evaluated. The average value of weight CV values of the tablets was 0.70%; the hardness of the tablets was 55 N; and the rate of reduction in the hardness of the tablets was 16%. The results are shown in Table 1.

The powder in this example was thought to be a powder having good flowability because of its smaller angle of repose and smaller compressibility than those of the powders of Examples 1 to 3. However, the tablets obtained from this powder had large weight variation during compression and low hardness.

Comparative Example 4

47.5 kg of crystalline cellulose CEOLUS PH-302 (manufactured by Asahi Kasei Chemicals Corp.; average degree of polymerization: 140, rate of particles remaining on a sieve of 250 μm in mesh size: 1% by mass, average L/D of particles of 75 μm or smaller: 1.3, bulk density: 0.417 g/cm$^3$, and angle of repose: 38°) as cellulose, 5.0 kg of acetaminophen (manufactured by API Corp.) as an active ingredient, and 47.5 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.40 kg of magnesium stearate (manufactured by Taihei Chemical Industrial Co., Ltd.) as a lubricant was further added to the V-type mixer and further mixed therewith at 23 rpm for 5 minutes to obtain a powder for use in compression.

The powder thus obtained had an angle of repose of 40°, a loose bulk density of 0.541 g/cm$^3$, a packed bulk density of 0.671 g/cm$^3$/and a compressibility of 19%. Moreover, the powder had a tensile elongation at break of 18 μm and required flow energy of 383 mJ during aeration.

A portion of this powder was used to measure a tensile elongation at break of the powder after passing through a stirring feeder, packing density into a die, and packing density during low-speed compression in the same way as in Example 1. As a result, the tensile elongation at break of the powder after passing through a stirring feeder was 18 μm; the packing density into a die was 1.27 times the loose bulk density; and the ratio of "the packing density during high-speed compression/the packing density during low-speed compression" was 0.973. The present powder was not sufficiently compacted even with the stirring feeder in high-speed compression.

The remaining powder was used and compressed for 3 consecutive hours using a rotary tablet machine (LIBRA) in the same way as in Example 1 to obtain tablets, which were evaluated. The average value of weight CV values of the tablets was 0.73%; the hardness of the tablets was 65 N; and the rate of reduction in the hardness of the tablets was 15%. The results are shown in Table 1.

The powder in this example was thought to be a powder having good flowability because of its smaller angle of repose and smaller compressibility than those of the powders of Examples 1 to 3. However, the tablets obtained from this powder had large weight variation during compression and low hardness.

Comparative Example 5

9.5 kg of crystalline cellulose CEOLUS KG-802 (manufactured by Asahi Kasei Chemicals Corp.; average degree of polymerization: 270, rate of particles remaining on a sieve of 250 μm in mesh size: 1% by mass, average L/D of particles of 75 μm or smaller: 3.0, bulk density: 0.196 g/cm$^3$, and angle of repose: 50°) as cellulose, 5.0 kg of acetaminophen (manufactured by API Corp.) as an active ingredient, and 85.5 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for compression.

The powder thus obtained had an angle of repose of 36°, a loose bulk density of 0.636 g/cm$^3$, a packed bulk density of 0.761 g/cm$^3$, and a compressibility of 16%. Moreover, the powder had a tensile elongation at break of 36 μm and required flow energy of 392 mJ during aeration.

A portion of this powder was used to measure a tensile elongation at break of the powder after passing through a stirring feeder, packing density into a die, and packing density during low-speed compression in the same way as in Example 1. As a result, the tensile elongation at break of the powder after passing through a stirring feeder was 54 μm; the packing density into a die was 1.31 times the loose bulk density; and the ratio of "the packing density during high-speed compression/the packing density during low-speed compression" was 0.962. The present powder was not sufficiently compacted even with the stirring feeder in high-speed compression.

The remaining powder was used and compressed for 3 consecutive hours using a rotary tablet machine (LIBRA) in the same way as in Example 1 to obtain tablets, which were evaluated. The average value of weight CV values of the tablets was 0.88%; the hardness of the tablets was 77 N; and the rate of reduction in the hardness of the tablets was 17%. The results are shown in Table 1.

The powder in this example was thought to be a powder having good flowability because of its smaller angle of repose and smaller compressibility than those of the powders of Examples 1 to 3. However, the tablets obtained from this powder had large weight variation during compression and low hardness.

Comparative Example 6

81.0 kg of crystalline cellulose CEOLUS KG-802 (manufactured by Asahi Kasei Chemicals Corp.; average degree of polymerization: 270, rate of particles remaining on a sieve of 250 μm in mesh size: 1% by mass, average L/D of particles of 75 μm or smaller: 3.0, bulk density: 0.196 g/cm$^3$, and angle of repose: 50°) as cellulose, 5.0 kg of acetaminophen (manufactured by API Corp.) as an active ingredient, and 16.0 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for compression.

The powder thus obtained had an angle of repose of 48°, a loose bulk density of 0.235 g/cm³, a packed bulk density of 0.425 g/cm³, and a compressibility of 45%. Moreover, the powder had a tensile elongation at break of 103 μm and required flow energy of 236 mJ during aeration.

A portion of this powder was used to measure a tensile elongation at break of the powder after passing through a stirring feeder, packing density into a die, and packing density during low-speed compression in the same way as in Example 1. As a result, the tensile elongation at break of the powder after passing through a stirring feeder was 125 μm; the packing density into a die was 1.47 times the loose bulk density; and the ratio of "the packing density during high-speed compression/the packing density during low-speed compression" was 0.955. The present powder was not sufficiently compacted even with the stirring feeder in high-speed compression.

The remaining powder was used and compressed for 3 consecutive hours using a rotary tablet machine (LIBRA) in the same way as in Example 1 to obtain tablets, which were evaluated. The average value of weight CV values of the tablets was 1.02%; the hardness of the tablets was 133 N; and the rate of reduction in the hardness of the tablets was 9%. The results are shown in Table 1.

A portion of the powder in this example blocked the stirring feeder portion because of its tensile elongation at break as large as 103 μm. Moreover, a portion of the powder caused clogging of a hopper. Therefore, the tablets obtained from this powder had large weight variation.

Comparative Example 7

19.0 kg of crystalline cellulose CEOLUS PH-F20 (trade name, manufactured by Asahi Kasei Chemicals Corp.; average degree of polymerization: 250, rate of particles remaining on a sieve of 250 μm in mesh size: 0% by mass, average L/D of particles of 75 μm or smaller: 2.0, bulk density: 0.230 g/cm³, and angle of repose: 60°) as cellulose, 5.0 kg of acetaminophen (manufactured by API Corp.) as an active ingredient, and 76.0 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for compression.

The powder thus obtained had an angle of repose of 41°, a loose bulk density of 0.494 g/cm³, a packed bulk density of 0.767 g/cm³, and a compressibility of 36%. Moreover, the powder had a tensile elongation at break of 187 μm and required flow energy of 330 mJ during aeration.

A portion of this powder was used to measure a tensile elongation at break of the powder after passing through a stirring feeder, packing density into a die, and packing density during low-speed compression in the same way as in Example 1. As a result, the tensile elongation at break of the powder after passing through a stirring feeder was 208 μm; the packing density into a die was 1.35 times the loose bulk density; and the ratio of "the packing density during high-speed compression/the packing density during low-speed compression" was 0.984. The present powder was compacted in the case of using the stirring feeder in high-speed compression.

However, when the remaining powder was used and compressed for 3 consecutive hours using a rotary tablet machine (LIBRA) in the same way as in Example 1, a phenomenon was seen in which the powder blocked a hopper outlet during the compression, resulting in unsuccessful compression. While the blockage was removed, compression was performed for 3 hours, albeit not consecutive, to obtain tablets, which were evaluated. The average value of weight CV values of the tablets was 1.13%; the hardness of the tablets was 81 N; and the rate of reduction in the hardness of the tablets was 15%. The results are shown in Table 1.

The powder in this example blocked the stirring feeder portion and caused clogging of a hopper because of its tensile elongation at break as very large as 187 μm. Therefore, continuous compression was difficult, and the tablets obtained from this powder had large weight variation.

Comparative Example 8

28.5 kg of crystalline cellulose CEOLUS KG-802 (manufactured by Asahi Kasei Chemicals Corp.; average degree of polymerization: 270, rate of particles remaining on a sieve of 250 μm in mesh size: 1% by mass, average L/D of particles of 75 μm or smaller: 3.0, bulk density: 0.196 g/cm³, and angle of repose: 50°) as cellulose, 55.0 kg of acetaminophen (manufactured by API Corp.) as an active ingredient, and 16.5 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for compression.

The powder thus obtained had an angle of repose of 49°, a loose bulk density of 0.297 g/cm³, a packed bulk density of 0.628 g/cm³, and a compressibility of 48%. Moreover, the powder had a tensile elongation at break of 18 μm and required flow energy of 393 mJ during aeration.

A portion of this powder was used to measure a tensile elongation at break of the powder after passing through a stirring feeder, packing density into a die, and packing density during low-speed compression in the same way as in Example 1. As a result, the tensile elongation at break of the powder after passing through a stirring feeder was 21 μm; the packing density into a die was 1.48 times the loose bulk density; and the ratio of "the packing density during high-speed compression/the packing density during low-speed compression" was 0.975. The present powder was not sufficiently compacted even with the stirring feeder in high-speed compression.

The remaining powder was used and compressed for 3 consecutive hours using a rotary tablet machine (LIBRA) in the same way as in Example 1 to obtain tablets, which were evaluated. The average value of weight CV values of the tablets was 0.98%; the hardness of the tablets was 60 N; and the rate of reduction in the hardness of the tablets was 13%. The results are shown in Table 1.

The powder in this example had a large angle of repose, a large compressibility, and a small tensile elongation at break, required large flow energy during aeration, and had unfavorable dynamic flowability.

Therefore, the tablets obtained from this powder had large weight variation during compression.

Comparative Example 9

28.5 kg of crystalline cellulose CEOLUS KG-802 (manufactured by Asahi Kasei Chemicals Corp.; average degree of polymerization: 270, rate of particles remaining on a sieve of 250 μm in mesh size: 1% by mass, average L/D of particles of 75 μm or smaller: 3.0, bulk density: 0.196 g/cm$^3$, and angle of repose: 50°) as cellulose, 5.0 kg of acetaminophen (manufactured by API Corp.) as an active ingredient, and 66.5 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for compression.

The powder thus obtained had an angle of repose of 42°, a loose bulk density of 0.454 g/cm$^3$, a packed bulk density of 0.628 g/cm$^3$, and a compressibility of 28%. Moreover, the powder had a tensile elongation at break of 45 μm and required flow energy of 307 mJ during aeration.

A portion of this powder for compression was used to measure packing density into a die and packing density during low-speed compression using an open feeder without use of a stirring feeder. As a result, the packing density into a die was 1.15 times the loose bulk density; and the ratio of "the packing density during high-speed compression/the packing density during low-speed compression" was 0.947. The present powder was not sufficiently compacted and had poor packability during high-speed compression, when compressed without use of a stirring feeder.

The remaining powder for compression was used and compressed for 3 consecutive hours using a rotary tablet machine (LIBRA) under the same conditions as in Examples except that an open feeder was used without performing compaction using a stirring feeder, to obtain tablets, which were evaluated. The average value of weight CV values of the tablets was 1.21%; the hardness of the tablets was 98 N; and the rate of reduction in the hardness was 11%. The results are shown in Table 1.

The tablets in this example had larger weight variation than that of Example 1. It was thus demonstrated that compression must be performed during compaction using a stirring feeder.

Comparative Example 10

28.5 kg of crystalline cellulose CEOLUS PH-302 (manufactured by Asahi Kasei Chemicals Corp.; average degree of polymerization: 140, rate of particles remaining on a sieve of 250 μm in mesh size: 1% by mass, average L/D of particles of 75 μm or smaller: 1.3, bulk density: 0.417 g/cm$^3$, and angle of repose: 38°) as cellulose, 5.0 kg of acetaminophen (manufactured by API Corp.) as an active ingredient, and 65.5 kg of granulated lactose SUPER-TAB (distributed by Asahi Kasei Chemicals Corp.) as an additive were added to a V-type mixer (V-200, manufactured by Tokuju Corp.) and mixed at the number of revolutions of 23 rpm for 30 minutes. Subsequently, 0.50 kg of magnesium stearate (manufactured by Taihei Chemical Industrial Co., Ltd.) as a lubricant was further added to the V-type mixer and further mixed therewith at 23 rpm for 5 minutes to obtain a powder for compression.

The powder thus obtained had an angle of repose of 33°, a loose bulk density of 0.629 g/cm$^3$, a packed bulk density of 0.729 g/cm$^3$, and a compressibility of 14%. Moreover, the powder had a tensile elongation at break of 17 μm and required flow energy of 415 mJ during aeration.

A portion of this powder was used to measure packing density into a die and packing density during low-speed compression using an open feeder without use of a stirring feeder. As a result, the packing density into a die was 1.10 times the loose bulk density; and the ratio of "the packing density during high-speed compression/the packing density during low-speed compression" was 0.945. The present powder was not sufficiently compacted and had poor packability, when compressed without use of a stirring feeder.

The remaining powder was used and compressed for 3 consecutive hours using a rotary tablet machine (LIBRA) under the same conditions as in Examples except that an open feeder was used without performing compaction using a stirring feeder, to obtain tablets, which were evaluated. The average value of weight CV values of the tablets was 0.76%; the hardness of the tablets was 83 N; and the rate of reduction in the hardness was 15%. The results are shown in Table 1.

The tablets in this example had larger weight variation and lower hardness than those of Example 1. It was thus demonstrated that a powder having the properties of the present invention is effectively compressed during compaction using a stirring feeder.

TABLE 1

| | | Example 1 | Example 2 | Example 3 | Comparative Example 1 | Comparative Example 2 | Comparative Example 3 | Comparative Example 4 |
|---|---|---|---|---|---|---|---|---|
| Crystalline cellulose | Grade | KG-802 | KG-802 | KG-802 | PH-302 | PH-102 | PH-200 | PH-302 |
| | Average degree of polymerization [-] | 270 | 270 | 270 | 140 | 250 | 230 | 140 |
| | Rate of particles remaining on sieve of 250 μm in mesh size [%] | 1.0 | 1.0 | 1.0 | 1.0 | 0.2 | 15.8 | 1.0 |
| | Average L/D of particles of 75 μm or smaller [-] | 3.0 | 3.0 | 3.0 | 1.3 | 1.3 | 1.2 | 1.3 |
| | Bulk density [g/cm$^3$] | 0.196 | 0.196 | 0.196 | 0.417 | 0.312 | 0.357 | 0.417 |
| | Angle of repose [°] | 50 | 50 | 50 | 38 | 40 | 35 | 38 |
| | Formulated amount [kg] | 28.5 | 47.5 | 25.5 | 28.5 | 28.5 | 28.5 | 47.5 |
| APAP [kg] | | 5.0 | 5.0 | 15.0 | 5.0 | 5.0 | 5.0 | 5.0 |
| SUPER-TAB [kg] | | 66.5 | 47.5 | 59.5 | 66.5 | 58.5 | 58.5 | 47.5 |
| MgSt [kg] | | 0.50 | 0.50 | 0.50 | 0.50 | 0.50 | 0.50 | 0.50 |
| Powder for high-speed direct compression | Angle of repose [°] | 42 | 45 | 43 | 33 | 34 | 32 | 40 |
| | Loose bulk density [g/cm$^3$] | 0.454 | 0.328 | 0.411 | 0.629 | 0.511 | 0.548 | 0.541 |
| | Packed bulk density [g/cm$^3$] | 0.628 | 0.509 | 0.623 | 0.729 | 0.702 | 0.650 | 0.671 |
| | Compressibility [%] | 28 | 36 | 34 | 14 | 28 | 16 | 19 |
| | Tensile elongation at break [μm] | 45 | 67 | 44 | 17 | 28 | 6 | 18 |
| | Flow energy during aeration [mJ] | 307 | 256 | 288 | 415 | 406 | 491 | 383 |
| Compacted (stirring feeder) | | ○ | ○ | ○ | ○ | ○ | ○ | ○ |
| Tensile elongation at break after passing through stirring feeder [μm] | | 70 | 82 | 62 | 10 | 30 | 1 | 18 |
| Powder immediately | Packing density of powder immediately before compression/loose | 1.51 | 1.61 | 1.56 | 1.25 | 1.29 | 1.18 | 1.27 |

TABLE 1-continued

| | | | | | | | | |
|---|---|---|---|---|---|---|---|---|
| before compression | bulk density [-] | | | | | | | |
| | Packing density during high-speed compression/packing density during low-speed compression [-] | 0.998 | 0.981 | 0.988 | 0.971 | 0.972 | 0.962 | 0.973 |
| Tablet evaluation | Weight CV value [%] | 0.54 | 0.59 | 0.58 | 0.74 | 0.73 | 0.70 | 0.73 |
| | Tablet hardness [N] | 92 | 104 | 85 | 72 | 78 | 55 | 65 |
| | Rate of reduction in hardness [%] | 12 | 10 | 8 | 17 | 15 | 16 | 15 |

| | | Comparative Example 5 | Comparative Example 6 | Comparative Example 7 | Comparative Example 8 | Comparative Example 9 | Comparative Example 10 |
|---|---|---|---|---|---|---|---|
| Crystalline cellulose | Grade | KG-802 | KG-802 | PH-F20 | KG-802 | KG-802 | PH-302 |
| | Average degree of polymerization [-] | 270 | 270 | 250 | 270 | 270 | 140 |
| | Rate of particles remaining on sieve of 250 μm in mesh size [%] | 1.0 | 1.0 | 0.0 | 1.0 | 1.0 | 1.0 |
| | Average L/D of particles of 75 μm or smaller [-] | 3.0 | 3.0 | 2.0 | 3.0 | 3.0 | 1.3 |
| | Loose bulk density [g/cm$^3$] | 0.196 | 0.196 | 0.230 | 0.196 | 0.196 | 0.417 |
| | Angle of repose [°] | 50 | 50 | 60 | 50 | 50 | 38 |
| | Formulated amount [kg] | 9.5 | 81.0 | 19.0 | 28.5 | 28.5 | 28.5 |
| APAP [kg] | | 5.0 | 5.0 | 5.0 | 55.0 | 5.0 | 5.0 |
| SUPER-TAB [kg] | | 58.5 | 16.0 | 76.0 | 16.5 | 66.2 | 58.5 |
| MgSt [kg] | | 0.50 | 0.50 | 0.50 | 0.50 | 0.50 | 0.50 |
| Powder for high-speed direct compression | Angle of repose [°] | 36 | 48 | 41 | 49 | 42 | 33 |
| | Loose bulk density [g/cm$^3$] | 0.636 | 0.235 | 0.494 | 0.297 | 0.454 | 0.629 |
| | Packed bulk density [g/cm$^3$] | 0.761 | 0.425 | 0.767 | 0.628 | 0.628 | 0.729 |
| | Compressibility [%] | 16 | 45 | 36 | 48 | 28 | 14 |
| | Tensile elongation at break [μm] | 36 | 103 | 187 | 18 | 45 | 17 |
| | Flow energy during aeration [mJ] | 392 | 236 | 330 | 393 | 307 | 415 |
| Compacted (stirring feeder) | | ○ | ○ | ○ | ○ | x | x |
| Tensile elongation at break after passing through stirring feeder [μm] | | 54 | 125 | 208 | 21 | — | — |
| Powder immediately before compression | Packing density of powder immediately before compression/loose Packing density [-] | 1.31 | 1.47 | 1.35 | 1.48 | 1.15 | 1.10 |
| | Packing density during high-speed compression/Packing density during low-speed compression [-] | 0.962 | 0.955 | 0.984 | 0.975 | 0.947 | 0.945 |
| Tablet evaluation | Weight CV value [%] | 0.88 | 1.02 | 1.13 | 0.98 | 1.21 | 0.76 |
| | Tablet hardness [N] | 77 | 133 | 91 | 60 | 98 | 83 |
| | Rate of reduction in hardness [%] | 17 | 9 | 15 | 13 | 11 | 15 |

INDUSTRIAL APPLICABILITY

A process for producing a tablet by high-speed direct compression according to the present invention can be utilized preferably for obtaining tablets having small weight variation and high hardness.

The invention claimed is:

1. A process for producing a tablet, characterized by comprising performing high-speed direct compression at a punch moving speed of 800 mm/s or more; while compacting a powder which comprises at least 15 to 80% by mass of cellulose, an active ingredient, and a lubricant and has an angle of repose of 50° or less, a compressibility of 20% or more, and a tensile elongation at break of 30 μm or more, wherein said powder is prepared without a fluidizer.

2. The process according to claim 1, wherein the cellulose is crystalline cellulose of which an average degree of polymerization is 150 to 450, a rate of particles remaining on a sieve of 250 μm in mesh size is 10% by mass or less, average L/D of particles of 75 μm or smaller is 2.0 or more, a bulk density is 0.25 g/cm$^3$ or less, and an angle of repose is 43° or more.

3. The process according to claim 1, wherein the powder requires flow energy of 400 mJ or less during aeration.

4. The process according to claim 3, wherein the powder requires flow energy of 350 mJ or less during aeration.

5. The process according to claim 1, wherein the powder has an angle of repose of 30 to 50°.

6. The process according to claim 1, wherein the powder has a compressibility of 20 to 50%.

7. The process according to claim 1, wherein the powder has a tensile elongation at break of 100 μm or less.

8. The process according to claim 3, wherein the powder requires flow energy of 100 mJ or more during aeration.

9. The process according to claim 1, wherein the compaction is performed with a stirring feeder attached to a tablet machine.

10. The process according to claim 2, wherein the powder requires flow energy of 400 mJ or less during aeration.

11. The process according to claim 10, wherein the powder requires flow energy of 350 mJ or less during aeration.

12. The process according to claim 2, wherein the powder has an angle of repose of 30 to 50°.

13. The process according to claim 2, wherein the powder has a compressibility of 20 to 50%.

14. The process according to claim 2, wherein the powder has a tensile elongation at break of 100 μm or less.

15. The process according to claim 11, wherein the powder requires flow energy of 100 mJ or more during aeration.

16. The process according to claim 10, wherein the compaction is performed with a stirring feeder attached to a tablet machine.

* * * * *

UNITED STATES PATENT AND TRADEMARK OFFICE
CERTIFICATE OF CORRECTION

| | | |
|---|---|---|
| PATENT NO. | : 8,106,100 B2 | Page 1 of 1 |
| APPLICATION NO. | : 12/086001 | |
| DATED | : January 31, 2012 | |
| INVENTOR(S) | : Kakizawa et al. | |

It is certified that error appears in the above-identified patent and that said Letters Patent is hereby corrected as shown below:

First Page Column 2 (Abstract), Line 6, Delete "50° C." and insert -- 50° --, therefor.

Column 27, Line 50 (Approx.), In Claim 1, delete "more;" and insert -- more --, therefor.

Signed and Sealed this
Fifteenth Day of May, 2012

David J. Kappos
*Director of the United States Patent and Trademark Office*